(12) United States Patent
Rastinehad et al.

(10) Patent No.: US 11,903,650 B2
(45) Date of Patent: Feb. 20, 2024

(54) METHOD FOR PROVIDING CLINICAL SUPPORT FOR SURGICAL GUIDANCE DURING ROBOTIC SURGERY

(71) Applicants: Ardeshir Rastinehad, New York, NY (US); Alberto Martini, Florence (IT)

(72) Inventors: Ardeshir Rastinehad, New York, NY (US); Alberto Martini, Florence (IT)

( * ) Notice: Subject to any disclaimer, the term of this patent is extended or adjusted under 35 U.S.C. 154(b) by 806 days.

(21) Appl. No.: 16/948,293

(22) Filed: Sep. 11, 2020

(65) Prior Publication Data
US 2021/0068900 A1 Mar. 11, 2021

Related U.S. Application Data

(60) Provisional application No. 62/898,880, filed on Sep. 11, 2019.

(51) Int. Cl.
| | |
|---|---|
| *A61B 34/10* | (2016.01) |
| *A61B 34/00* | (2016.01) |
| *A61N 5/10* | (2006.01) |
| *G16H 10/60* | (2018.01) |
| *A61B 34/35* | (2016.01) |
| *G16H 30/20* | (2018.01) |

(52) U.S. Cl.
CPC .............. *A61B 34/10* (2016.02); *A61B 34/25* (2016.02); *A61B 34/35* (2016.02); *A61N 5/1039* (2013.01); *G16H 10/60* (2018.01); *G16H 30/20* (2018.01); *A61B 2034/107* (2016.02)

(58) Field of Classification Search
CPC ......... A61B 34/10; A61B 34/25; A61B 34/35; A61B 2034/107; A61N 5/1039; G16H 10/60; G16H 30/20; G16H 20/40

USPC ......................................................... 382/128
See application file for complete search history.

(56) References Cited

U.S. PATENT DOCUMENTS

| | | | |
|---|---|---|---|
| 5,713,350 | A | 2/1998 | Yokota et al. |
| 5,817,022 | A | 10/1998 | Vesely |
| 5,877,819 | A | 3/1999 | Branson |
| 6,256,529 | B1 | 7/2001 | Holupka et al. |
| 8,384,771 | B1 | 2/2013 | Douglas |
| 8,992,231 | B2 | 3/2015 | Betrouni et al. |
| 9,101,397 | B2 | 8/2015 | Guthart et al. |
| 9,218,053 | B2 | 12/2015 | Komuro et al. |
| 9,349,183 | B1 | 5/2016 | Douglas et al. |
| 9,402,690 | B2 | 8/2016 | Zhao et al. |
| 9,473,766 | B2 | 10/2016 | Douglas et al. |
| 9,492,240 | B2 | 11/2016 | Itkowitz et al. |
| 9,858,665 | B2 | 1/2018 | Metzger et al. |
| 9,980,691 | B2 | 5/2018 | Douglas et al. |
| 10,258,425 | B2 | 4/2019 | Mustufa et al. |
| 10,292,678 | B2 | 5/2019 | Naidu et al. |
| 10,507,066 | B2 | 12/2019 | DiMaio et al. |
| 10,565,479 | B1 | 2/2020 | Lesniak |
| 2005/0154288 | A1 | 7/2005 | Wang et al. |
| 2005/0204310 | A1 | 9/2005 | De Zwart et al. |
| 2008/0004603 | A1 | 1/2008 | Larkin et al. |
| 2008/0033240 | A1 | 2/2008 | Hoffman et al. |
| 2009/0262988 | A1 | 10/2009 | Karkanias et al. |

(Continued)

FOREIGN PATENT DOCUMENTS

WO 2018175094 A1 9/2018

*Primary Examiner* — Huy C Ho
(74) *Attorney, Agent, or Firm* — Dunlap Bennett & Ludwig, PLLC

(57) ABSTRACT

A method for providing clinical support for surgical guidance during robotic surgery.

12 Claims, 1 Drawing Sheet

(56) References Cited

U.S. PATENT DOCUMENTS

| | | |
|---|---|---|
| 2013/0211230 A1 | 8/2013 | Sperling |
| 2014/0073907 A1* | 3/2014 | Kumar ............... A61B 10/0241 |
| | | 600/407 |
| 2014/0176661 A1* | 6/2014 | Smurro ................. G16H 20/40 |
| | | 348/14.06 |
| 2016/0027178 A1 | 1/2016 | Yu et al. |
| 2016/0038247 A1 | 2/2016 | Bharadwaj et al. |
| 2017/0084022 A1 | 3/2017 | Naidu et al. |
| 2017/0281233 A1 | 10/2017 | Edelhauser et al. |
| 2018/0047183 A1 | 2/2018 | Berlinger et al. |
| 2018/0082480 A1 | 3/2018 | White et al. |
| 2018/0227352 A1 | 8/2018 | Ortiz et al. |
| 2020/0214619 A1 | 7/2020 | Leng et al. |

\* cited by examiner

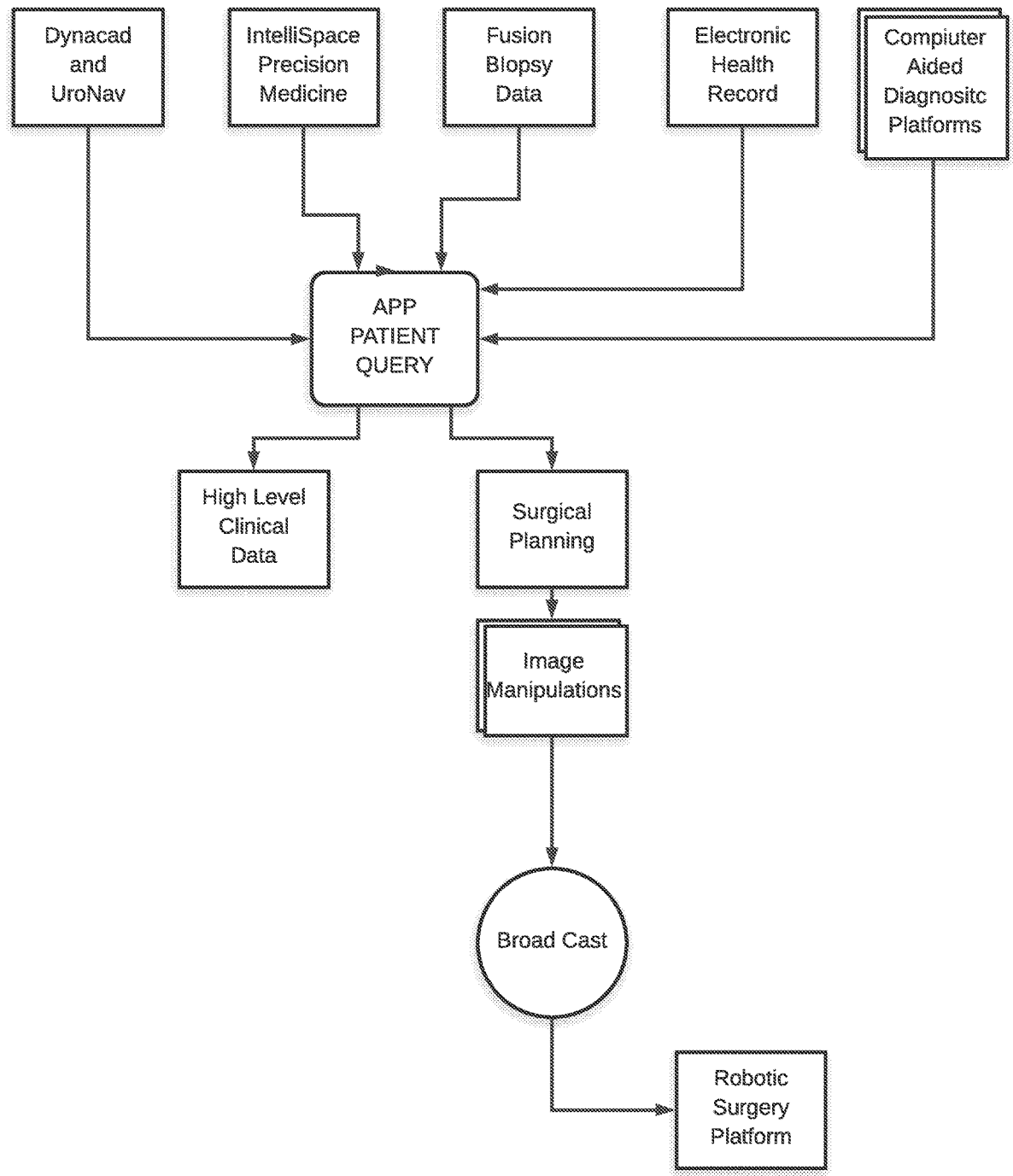

METHOD FOR PROVIDING CLINICAL SUPPORT FOR SURGICAL GUIDANCE DURING ROBOTIC SURGERY

CROSS-REFERENCE TO RELATED APPLICATION

This application claims the benefit of priority of U.S. provisional application No. 62/898,880, filed 11 Sep. 2019, the contents of which are herein incorporated by reference.

BACKGROUND OF THE INVENTION

The present invention relates to robotic surgical procedures and, more particularly, a computer-implemented method for providing clinical support for surgical guidance during robotic surgery.

MRIs contain crucial information for surgical planning. In fact, the use of the three-dimensional (3D) models obtained from multiparametric MRI (mpMRI) has become the standard of care in the United Kingdom and in Europe for staging of prostate cancer. In the United States, the National Clinical Cancer Network has also added the use of mpMRI in the screening and staging of prostate cancer.

The surgeon's skill level to interpret mpMRI, however, has not kept pace with the proliferation of mpMRI of the prostate. Generally speaking, surgeons have a limited understanding of intra-operative prostate anatomy correlated with mpMRI of the prostrate since mpMRI is new for urologist and there is no residency training to interpret MRIs, and currently no way to actively use mpMRI information during surgery. As a result, the surgeons are unable to use the valuable information to improve or tailor their surgical approach; for instance, to avoid cutting through tumors during surgery.

Prostate cancer is the most common male malignancy and one man out of seven will be diagnosed with prostate cancer during his lifetime. Radical prostatectomy, that represents the surgical extirpation of the cancer, is performed by means of robotic surgery in the vast majority of the hospitals in the USA.

In 2009 the FDA cleared the first device that could use information from an MRI to guide a biopsy using technology that merges the ultrasound and MRI data sets to guide the prostate biopsy. There is level 1 evidence (2019) that this new approach is superior to the prior ultrasound only biopsy approach. In 2013, the commercial systems became available in the United States. The pathology results and 3D data from these biopsy approaches can be stored and reviewed prior to the surgical treatments using customized workstations. A key component is that these data points were not available until 2013 and that each biopsy core is tracked and recorded in 3D space. This data, which includes cancer location and extension, is then matched back to the mpMRI of the prostate and a 3D map of a patient's prostate and critical structures can be created.

One of the goals of the surgical treatment for prostate cancer (PCa), along with oncological control, is to provide patients with optimal quality of life. In an effort to achieve that, surgeons must attempt a "conservative" dissection allowing for maximal preservation of the structures surrounding the prostate, including the neurovascular bundles. The extent of the dissection will ultimately influence urinary continence and erectile function.

Considering the fact that surgeons walk on a fine line trying to balance the risk of extra-prostatic disease and the risk of resecting through tumorous tissue, the frequency of Post-Surgical Margins (PSM) is higher in men diagnosed with prostate cancer relative to those diagnosed with other malignancies. For instance, compared to the most common female malignancy, i.e., breast cancer, the PSM rate in surgically treated PCa is almost four times higher.

In short, the urologist requires the expertise of a radiologists to decipher MR Images to help them tailor their surgical plan, yet the current information that urologist require during surgery are unfortunately available in multiple different, disparate software systems within the hospital. These systems may provide the information, but most surgeons lack the skill and expertise to maximize surgical performance. In other words, the information to aid these surgeons is available; however, the information is not accessible during robotic surgery.

The utilization of 3D models at the time of surgery can provide surgeons with visual information denoting the location of the tumor—offering the potential not only to tailor to each patient the best surgical approach but also to reduce PSMs, which occur anytime a surgeon cuts through a tumor and leaves a piece of malignant tissue inside the human body. Also, there is currently no computer-based or software-based solution allowing clinical/imaging data to be available to surgeons during real time surgery on the robotic console.

As can be seen, there is a need for a computer-implemented method for providing clinical support for surgical guidance during robotic surgery. The present invention will draw information from the diagnostic radiology studies, 3D MR US fusion guided biopsy data, clinical variables and allow it to be accessed during surgery through a software application interface that broadcasts visual information into the robotic surgery platform and provides a controller for manipulating data in real-time. Thereby, the present invention integrates 3D modules obtained from mpMRIs in the robotic console at the time of surgery to assist with predicting extra-prostatic extension; defining large tumor volume abutting the capsule; identifying the location of the tumor; optimizing nerve dissection; and providing surgeons with a visual tool during the dissection phase of robot-assisted radical prostatectomy.

The data will be accessed, and never stored, on a portable device, such as, but not limited to, a smartphone, tablet or laptop, connected to the healthcare internal network. The data will be available on the device; this device will be streaming the information to the robotic console for enhancing surgical planning and improving surgery performance. The data will not be modified; rather, the sole role of the portable device is to display data. Images and patient data will never be modified during surgery. Under no circumstances will the process embodied in the present invention interfere with the functions of the robotic system. The data will be displayed in the screen of the robotic console.

One example of a medical robotic system is the daVinci® Surgical System from Intuitive Surgical, Inc., of Sunnyvale, CA. The daVinci® system includes a surgeon's console, a patient-side cart, a high performance 3-D vision system, and Intuitive Surgical's proprietary EndoWrist™ articulating instruments. In this system, the TilePro™ function, which is a default function of the surgical console allows to split the screen in parts for a multi-input display of information.

The aforementioned data will be displayed in one of the parts of the screen of the console and never superimposed to the images that originate from the patient's body. If using the daVinci® system, the data will be displayed using the TilePro™ function; if using another robotic system, the data will be displayed through their split screen function.

Considering robotic surgery is an inherently computer-based field, the computer-implemented method for providing clinical support for surgical guidance during robotic surgery would improve this technological field and related fields such as robotic consoles, surgical interfaces and the like.

The present invention applies also to robotic surgical procedures that are performed on any parenchymal or hollow organ or robotic surgical procedures in general whenever preoperative imaging planning is deemed appropriate by the treating physician.

SUMMARY OF THE INVENTION

In one aspect of the present invention, a system for providing clinical support for a surgery includes the following: a processor; a display device to display one or more real time images originating from a selected patient; and a memory having computing device-executable instructions that, when executed by the processor, cause the processor to implement: a communications interface for accessing a magnetic resonance imaging data and an electronic health record data for the selected patient over a network, wherein said data is accessed but never stored; a user interface for displaying and interacting with the communications interface; and a generation module for broadcasting the user interface on the display device juxtaposed to said one or more real time images, whereby the user interface is never superimposed on the one or more real time images.

In another aspect of the present invention, the system for providing clinical support for a surgery a processor; a surgical console having to display one or more real time images originating from a selected patient; and a memory having computing device-executable instructions that, when executed by the processor, cause the processor to implement: a communications interface for accessing a magnetic resonance imaging data and a fusion biopsy data set for the selected patient over a network, wherein said data is accessed but never stored, and wherein the magnetic resonance imaging data and the electronic health record data comprise a preoperative imaging plan; a user interface for displaying and interacting with the communications interface; and a generation module for broadcasting the user interface on the surgical console in such a way that the user interface is juxtaposed to said one or more real time images, wherein the magnetic resonance imaging data comprises a three dimensional model configured to be rotatable about a three-dimensional axis, and wherein the three-dimensional model configured to provide zoom functionality and highlighting functionality, whereby the user interface is never superimposed on the one or more real time images, wherein the user interface is displayed along one screen of a split-screen functionality generated by the generation module, and wherein the display device has an integrated broadcasting device for receiving the user interface.

These and other features, aspects and advantages of the present invention will become better understood with reference to the following drawings, description and claims.

BRIEF DESCRIPTION OF THE DRAWINGS

The sole FIGURE is a flow chart of an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Referring now to the sole FIGURE, the present invention may include at least one computer with a user interface. The computer may include at least one processing unit coupled to a form of memory. The computer may include, but not limited to, a microprocessor, a server, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser. The computer may access the systemic software application via the web browser using the internet, extranet, intranet, host server, internet cloud and the like.

A method of using the present invention may include the following. The systemic software application enables the user-medical professional to select a patient to be queried through the present invention's 'Patient for Surgery' modality. The systemic software application then queries the Application Programming Interfaces (API) for all hospital-based systems, such as Dynacad, IntelliSpace Precision Medicine, Computer Aided diagnostic systems, UroNav, fusion biopsy platforms, and the like for electronic health record data for the selected patient. The systemic software application may be adapted to extract relevant data points which can include, but are not limited to, demographic, lab values, and 3D data from Dynacad and electronic medical records from the aforementioned platforms. The systemic software application is configured to be HIPAA and HITRUST compliant.

The data will then be retrieved and then displayed for the user on a display screen for selective manipulation for surgical planning via the system software application. Specifically, in certain embodiments, during manipulation the data is broadcast/transmitted to the robotic console via the robotics DVI port or broadcast/transmitted directly to a robotic console having an integrated broadcasting device. The user will be able to see current demographic, prostate cancer information and select a Surgical Planning Tool modality. The Surgical Planning Tool includes a three-dimensional model of the prostatic gland and the prostate tumor that can be rotated on the three-dimensional axis (x, y and z) and can be zoomed in or out. The orientation can be adjusted to present surgical views to aid with bladder neck dissection, nerve sparing approach, and urethral sphincter mobilization. In the model, area(s) with the tumor will be identifiable in part through a different color, relative to the "healthy" prostatic parenchyma, i.e. area of the prostate devoid of tumor. Users are able to highlight different areas of risk, e.g., the urethra, rectum, previous positive biopsy cores, areas of possible extra-prostatic extension, seminal vesicles, vasa deferentia and other anatomical structures.

The content of the systemic software application, that is displayed on the screen of the smartphone, will be broadcast to the robotic surgical platform. The broadcasting will be realized by means of, but not limited to, Google Chromecast, Amazon Firestick and Apple TV, S-video, DVI, HDMI.

The systemic software application enables a server-based software solution accessing multiple data systems while organizing and presenting the data to the surgeon in the operating theatre by way of a consolidation module coupling a systemic user interface and the robotic console. The systemic software application may be coded in 10S, Android, React native and or web-based platform. The systemic software application may act as a conduit for information between hospital based EMR, computer aided diagnostic systems, and biopsy platforms while combining the information for transmission, display, orientation during robotic surgery on the robotic surgery platform. The systemic software application could be used for other surgical navigation using 3D imaging for surgical planning.

The system includes at least one computing device having a processor and a memory. The memory includes software in the form of computing device-executable instructions that, when executed by the processor, cause the processor to implement: a communications interface, a user interface, and a consolidation module.

The computing device is at least the processor and the memory. The computing device may include a smart phone, a tablet computer, a laptop, a desktop, and the like. The computing device may execute on any suitable operating system such as IBM's zSeries/Operating System (z/OS), MS-DOS, PC-DOS, MAC-iOS, WINDOWS, UNIX, OpenVMS, ANDROID, an operating system based on LINUX, or any other appropriate operating system, including future operating systems.

In particular embodiments, the computing device includes the processor, the memory, the user interface, and the communication interface. In particular embodiments, the processor includes hardware for executing instructions, such as those making up a computing device program. The memory includes main memory for storing instructions such as computing device program(s) for the processor to execute, or data for processor to operate on. The memory may include an HDD, a floppy disk drive, flash memory, an optical disc, a magneto-optical disc, magnetic tape, a Universal Serial Bus (USB) drive, a solid-state drive (SSD), or a combination of two or more of these. The memory may include removable or non-removable (or fixed) media, where appropriate. The memory may be internal or external to the computing device, where appropriate. In particular embodiments, the memory is non-volatile, solid-state memory.

The user interface is for displaying and interacting with communication interface. The user interface includes hardware, software, or both providing one or more interfaces for user communication with the computing device. As an example and not by way of limitation, the user interface may include an input-output device, keyboard, keypad, microphone, monitor, mouse, printer, scanner, speaker, still camera, stylus, tablet, touchscreen, trackball, video camera, another user interface or a combination of two or more of these.

The communications interface is for broadcasting to a virtual collaboration platform over a network. The communication interface includes hardware, software, or both providing one or more interfaces for communication (e.g., packet-based communication) between the computing device and one or more other computing devices on one or more networks. As an example and not by way of limitation, communication interface may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface. As an example and not by way of limitation, the computing device may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, the computing device may communicate with a wireless PAN (WPAN) (e.g., a BLUETOOTH WPAN), a WI-FI network, a WI-MAX network, a cellular telephone network (e.g., a Global System for Mobile Communications (GSM) network), or other suitable wireless network or a combination of two or more of these. The computing device may include any suitable communication interface for any of these networks, where appropriate.

A method and apparatus for retrieving accessing and storing medical data relating to a patient during a medical procedure. The invention provides a single interface to many disparate forms of medical data which is accessible over a local area network; wide area network direct connection or combinations thereof. In one embodiment an operating room control system for use during a medical procedure on a patient includes an input device a display device and a controller that is coupled to the input device and the display device. The controller receives one or more user inputs transmits a command to a server located outside of the operating room to retrieve medical data receives the medical data from the server and displays the medical data on the display device. Medical data can be captured by the controller using for example a camera and a video/image capture board keyboard and microphone during surgery or examination of the patient. The captured medical data can be stored on one or more remote servers as part of the patient records.

To assist a surgeon performing a medical procedure auxiliary images generally indicating internal details of an anatomic structure being treated are displayed and manipulated by the surgeon on a computer display screen to supplement primary images generally of an external view of the anatomic structure. A master input device controlling a robotic arm in a first mode may be switched by the surgeon to a second mode in order to function instead as a mouse-like pointing device to facilitate the surgeon performing such auxiliary information display and manipulation.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

It should be understood, of course, that the foregoing relates to exemplary embodiments of the invention and that modifications may be made without departing from the spirit and scope of the invention as set forth in the following claims.

What is claimed is:

1. A system for providing clinical support for a surgery comprising:
   a processor;
   a display device configured to display one or more real time images originating from a selected patient; and
   a memory comprising computing device-executable instructions that, when executed by the processor, cause the processor to implement:
      a communications interface for accessing a magnetic resonance imaging data and a fusion biopsy data for the selected patient over a network, wherein said data is accessed but never stored;
      a user interface for interacting with the communications interface for displaying the magnetic resonance imaging data and the fusion biopsy data, wherein said data is unmodified and not superimposed over other imagery after accessing said data from over the network a generation module for broadcasting the user interface on the display device in such a way that the user interface is juxtaposed to said one or more real time images,
   whereby the user interface is never superimposed on the one or more real time images.

2. The system of claim 1, wherein the magnetic resonance imaging data comprises a three-dimensional model configured to be rotatable about a three-dimensional axis.

3. The system of claim 2, wherein the three-dimensional model configured to provide zoom functionality and highlighting functionality.

4. The system of claim 1, wherein the user interface is displayed along one screen of a split-screen functionality generated by the generation module.

5. The system of claim 1, wherein the display device has an integrated broadcasting device for receiving the user interface.

6. The system of claim 1, wherein the communications interface is configured for accessing a preoperative imaging plan for the selected patient over the network, and wherein the preoperative imaging plan is displayed on the user interface.

7. The system of claim 1, wherein the display device is a surgical console.

8. The system of claim 1, wherein the display device is a robotic console.

9. The system of claim 1, wherein the display device is a robotic console for guiding prostatic surgery.

10. A system for providing clinical support for a surgery comprising:
    a processor;
    a surgical console configured to display one or more real time images originating from a selected patient; and
    a memory comprising computing device-executable instructions that, when executed by the processor, cause the processor to implement:
       a communications interface for accessing a magnetic resonance imaging data and a fusion biopsy data set for the selected patient over a network, wherein said data is accessed but never stored, and wherein the magnetic resonance imaging data and the electronic health record data comprise a preoperative imaging plan;
       a user interface for displaying the magnetic resonance imaging data and the fusion biopsy data set and interacting with the communications interface; and
       a generation module for broadcasting the user interface on the surgical console in such a way that the magnetic resonance imaging data and the fusion biopsy data set displayed on the user interface is juxtaposed to said one or more real time images, wherein the magnetic resonance imaging data comprises a three dimensional model configured to be rotatable about a three-dimensional axis, and wherein the three-dimensional model configured to provide zoom functionality and highlighting functionality,
    whereby the user interface is never superimposed on the one or more real time images.

11. The system of claim 10, wherein the user interface is displayed along one screen of a split-screen functionality generated by the generation module.

12. The system of claim 10, wherein the display device has an integrated broadcasting device for receiving the user interface.

* * * * *